United States Patent [19]

Delorme et al.

[11] Patent Number: 5,510,553
[45] Date of Patent: Apr. 23, 1996

[54] CATALYTIC DEHYDROGENATION OF ALKYLAROMATIC HYDROCARBONS

[75] Inventors: Luc F. L. Delorme, Waterloo; Francisco M. M. Cerejo, Ecaussines; Jacques F. Grootjans, Leefdaal, all of Belgium

[73] Assignee: Fina Research, S.A., Feluy, Belgium

[21] Appl. No.: 336,953

[22] Filed: Nov. 10, 1994

Related U.S. Application Data

[63] Continuation-in-part of Ser. No. 153,008, Nov. 12, 1992, abandoned, which is a continuation of Ser. No. 520,575, May 8, 1990, abandoned.

[30] Foreign Application Priority Data

May 12, 1989 [BE] Belgium .............................. 08900512

[51] Int. Cl.$^6$ .................. C07C 2/64; C07C 4/06
[52] U.S. Cl. .................. 585/444; 585/440; 585/445; 502/41; 502/66; 502/74
[58] Field of Search .............................. 585/444

[56] References Cited

U.S. PATENT DOCUMENTS

| | | | |
|---|---|---|---|
| 3,711,569 | 1/1973 | Tschopp et al. | 260/683.3 |
| 3,856,881 | 12/1974 | Manning | 260/680 E |
| 4,039,601 | 8/1977 | Soderquist et al. | 260/669 R |
| 4,152,300 | 5/1979 | Riesser | 252/462 |

*Primary Examiner*—Sharon Gibson
*Attorney, Agent, or Firm*—Michael J. Caddell; M. Norwood Cheaiers

[57] ABSTRACT

Alkylaromatic hydrocarbons are dehydrogenated into alkenylaromatic hydrocarbons by contacting them in the absence of molecular oxygen with a supported catalyst of the redox type wherein the metal in the catalyst is at a valency such that it is not in its most reduced state, and the catalyst is regenerated before being contacted with fresh feed.

10 Claims, 1 Drawing Sheet

CATALYTIC DEHYDROGENATION OF ALKYLAROMATIC HYDROCARBONS

CROSS REFERENCES TO RELATED APPLICATIONS

This application is a continuation-in-part of a prior application, Ser. No. 08/153,008, filed Nov. 12, 1992, entitled "Catalytic Dehydrogenation of Alkylaromatic Hydrocarbons", now abandoned; which prior application is a continuation application of a first prior application, Ser. No. 07/520,575, filed May 8, 1990, entitled "Catalytic Dehydrogenation of Alkylaromatic Hydrocarbons", now abandoned.

FIELD OF THE INVENTION

The present invention relates to a process for the catalytic dehydrogenation of hydrocarbons. Particularly the present invention relates to the dehydrogenation of alkylaromatic hydrocarbons to produce the corresponding alkenylaromatic hydrocarbons. More particularly the process of the invention uses catalytic systems of the redox type.

BACKGROUND OF THE INVENTION

Catalytic dehydrogenation of hychocarbons has been carried out for many years and constitutes an important catalytic process in view of the increasing demand for dehydrogenated products which may be utilized in their many various forms in products such as high octane gasolines, plastic materials and synthetic rubbers.

In the field of dehydrogenation of alkylaromatic hydrocarbons, known processes include thermal dehydrogenation, catalytic dehydrogenation in the presence of an inert diluent such as steam, and oxidative dehydrogenation, the latter involving the injection of molecular oxygen into the reaction medium. Although oxidative dehydrogenation may have the same advantages regarding reaction yield and selectivity of the desired product, it is also well known that the presence of molecular oxygen in the reaction medium leads to the formation of undesirable oxidation products such as aldehydes.

In order to partially obviate these drawbacks, it has been proposed to use very specific catalysts having a particular selectivity towards oxidation dehydrogenation of certain hydrocarbons whether or not of the alkylaromatic type.

In this respect, U.S. Pat. No. 4,777,319 to Kung, et al. teaches the use of vanadates or molybdenates for the selective dehydrogenation of paraffinic hydrocarbons having from 3 to 6 carbon atoms. However, the dehydrogenation reaction must be carried out in the presence of molecular oxygen, which displaces the thermodynamic equilibrium but leads to the formation of undesirable secondary oxidation products.

It has also been proposed in U.S. Pat. No. 4,742,180 to Gaffney to use supported catalysts, the support being essentially an oxide of praseodymium on which there is deposited an alkaline metal having a dehydrogenation action. However, the limited availability of praseodymium oxide for the production of huge amounts of alkenylaromatic hydrocarbons is a distinct disadvantage. Moreover, it should be noted that no significant result is indicated for the dehydrogenation of alkylaromatic hydrocarbons. Oganowski [Bulletin Polish Acad. Sci., Chemistry 31 (1983), pp. 129, 139, 153; J. Mol. Catal. 29 (1985) 109.] has also proposed use a catalyst of the $Mg_3(VO_4)_2$ type for the dehydrogenation of ethylbenzene, but the reaction must occur in the presence of a gas containing molecular oxygen. Moreover, it is known that oxides of the $V_2O_5$ type lead to a reaction of complete combustion of the hydrocarbon feed to $CO_2$ and $H_2$ when used in the dehydrogenation reaction of hydrocarbons in the absence of molecular oxygen. This results in loss of production (low selectivity) and lowered yields. [See U.S. Pat. No. 4,816,243 to Bradzil et al.]

An object of the present invention is to provide an improved process for the catalytic dehydrogenation of alkylaromatic hydrocarbons in the presence of a redox catalytic system.

Another object of the present invention is to provide an improved process for the catalytic dehydrogenation of alkylaromatic hydrocarbons in the absence of molecular oxygen.

A further object of the present invention is to provide an improved process for the catalytic dehydrogenation of alkylaromatic hydrocarbons in the presence of a redox catalytic system, whether or not supported, and of which one or more oxidation stages show a dehydrogenating activity.

SUMMARY OF THE INVENTION

The present invention provides for a process for the catalytic dehydrogenation of alkylaromatic hydrocarbons into corresponding alkenylaromatic hydrocarbons, which process comprises:

contacting the hydrocarbon feedstock to be dehydrogenated under dehydrogenation conditions, in the absence of any gas containing molecular oxygen, with a catalyst consisting of a reducible oxide of vanadium supported on a material selected from clays, zeolitic materials of the metallo-silicate or metallo-alumino-phosphate type, and oxides of a second metal selected from Ti, Zr, Zn, Th, Mg, Ca, Ba, Si and Al, said catalyst having a dehydrogenation activity when said vanadium has a valency such that it is not in its most reduced state, recovering the dehydrogenated hydrocarbons, regenerating the used catalyst, and contacting the regenerated catalyst with fresh hydrocarbon feedstock to be dehydrogenated.

DESCRIPTION OF THE PREFERRED EMBODIMENTS

Figure 1:
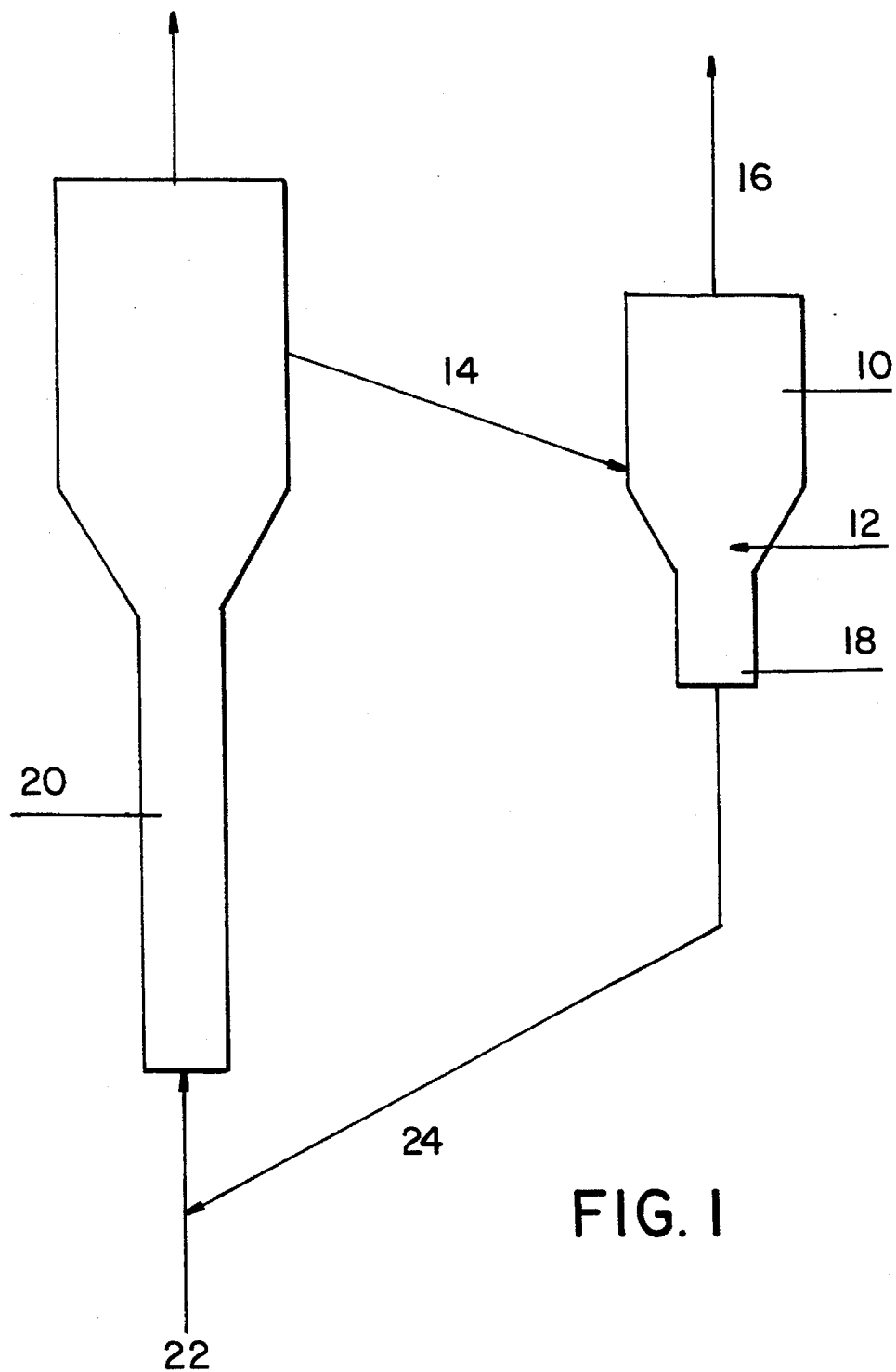
FIG. 1 is a schematic diagram of the reaction zone and regeneration zone utilizing the present invention process.

Applicants have found that with the process of this invention, the presence of molecular oxygen to perform the dehydrogenation reaction is no longer necessary, this fact constituting an important advantage over the prior processes.

According to the process of the present invention, the feedstock of alkylaromatic hydrocarbons to be dehydrogenated is contacted with the catalyst which has to fulfill several conditions. The catalyst comprises a reducible oxide of vanadium. Reducible oxide as used herein means an oxide of vanadium which is reduced by contact with hydrocarbons, when operating under dehydrogenation conditions. Moreover, the vanadium oxide used has to have a dehydrogenating action under the reaction conditions.

Further, it has been found that it is advantageous that these oxides be deposited on a support. By way of examples of suitable supports are the oxides of metals selected from Ti, Zr, Zn, Mg, Th, Si, Ca, Ba, and Al, together with clays, and zeolitic materials of the metallo-silicate or metallo-aluminophosphate type. Within the latter type are the aluminosilicates, the boresilicates, silico-alumino-phosphates and other analogs.

The supported catalyst used in the process of the invention may also comprise promoters such as alkali or alkaline-earth metals.

The supported catalyst may be prepared according to usual methods such as absorption, precipitation or still impregnation.

One specific catalyst which may be advantageously used in the process of the present invention, is a reducible vanadium oxide deposited on a support comprising magnesium oxide.

The contact between the feedstock to be dehydrogenated and the catalyst may be achieved in different ways; for instance the catalyst particles may be used in a fixed bed, or they may be used in a fluidized bed reactor wherein said particles are circulated and thereafter recovered. Preferably, the catalyst has sufficient particle size, good mechanical strength, and spherical shape to perform well in the fluidized bed reactor.

According to one embodiment of the present invention, the catalyst is placed in a fixed bed and contacted with a feedstock of alkylaromatic hydrocarbons to be dehydrogenated, in the absence of a molecular oxygen, at a temperature between about 300° and about 800° C., in order to maintain the feedstock in the vapor phase. When the activity of the catalyst is reduced over the limits which are currently acceptable, generally a reduction of about 10% in the conversion rate, feedstock contact with the catalyst is stopped and an air stream is passed over the catalyst bed at a temperature of from about 200° C. to about 1000° C. to regenerate the catalyst under mild conditions. This regeneration achieves at least a mild oxidation of the catalyst. After the catalyst is regenerated, the feedstock contact with the catalyst is resumed.

In a preferred embodiment of the present invention. The catalyst particles, whose sizes ranges from about 0.02 to about 0.30 mm, the catalyst being utilized in an oxidized form, are circulated in the dehydrogenation zone, and contacted with the feedstock to be dehydrogenated, in the absence of molecular oxygen. The process is preferably carried out at a temperature between about 300° and about 800° C. in order to maintain the feedstock in the vapor phase. The gas pressure at the outlet of the reactor is between about 10 and about 1.3×10 Pa, while residence time of the feedstock in the reactor is about 0.5 to about 15 seconds. The residence time of the catalyst is between about 0.5 second and about 5 minutes; the upper limit of the residence time of the catalyst being dependent upon its activity. According to this preferred embodiment, the dehydrogenation reaction and the transportation of the catalyst to the regenerator are preferably carried out in a fluidized bed reactor.

The catalyst in the reactor effluent is separated from the hydrocarbon effluent by suitable means, such as in a cyclone separator. The separated catalyst is a reduced catalyst because it is in a lower oxidation state than that of the fresh catalyst which enters the reaction zone. The separated catalyst is sent to a regeneration zone where it is regenerated with a gaseous stream containing molecular oxygen. This regeneration achieves at least a mild oxidation of the catalyst. The temperature in the regeneration zone is most often maintained between about 200° and about 1000° C.; the residence time of the catalyst in said zone is about 5 seconds to about 5 minutes, while that of the gas containing molecular oxygen is about 1 to about 30 seconds. The amount of gas, together with the oxygen concentration, must be sufficient to reoxidize the catalyst to its initial form. If this embodiment is used for the regeneration of the catalyst, then the dehydrogenation process may be carried out continuously, which was not the case in the previous embodiment.

The process of the invention is suitable for the dehydrogenation of alkylaromatic hydrocarbons into corresponding alkenylaromatic hydrocarbons. Particularly, the process of the invention is suitable for the catalytic dehydrogenation of ethylbenzene and ethyltoluene into styrene and vinyltoluene, respectively. The process is generally carried out at a temperature between about 350° and 800 ° C. and preferably between 400° and 650° C., at a pressure of between about 0.001 and about 1 MPa and at a hourly space velocity between about 0.01 and about 10.0 Kg of hydrocarbon per hour and per Kg of catalyst.

The preferred embodiment of the invention is also described by way of the drawing in which FIG. 1 represents a schematic diagram of the reaction zone and the regeneration zone for the catalyst.

Referring now to FIG. 1, there is illustrated a dehydrogenation reactor 10 wherein the feedstock of hydrocarbons to be dehydrogenated enters through pipe 12 while catalyst in oxidized forms enters through pipe 14. Dehydrogenated hydrocarbons are withdrawn through pipe 16 while reduced catalyst is collected in area 18 of the dehydrogenation reactor and transported to the bottom of regeneration reactor 20. A gas heated to the aforementioned regeneration temperature range and containing molecular oxygen is introduced into pipe 22 while the reduced catalyst is introduced through pipe 24 into regeneration reactor 20. Regenerated catalyst is recovered in the outlet pipe 14 and transported in oxidized form to the dehydrogenation reactor 10.

The process of the present invention shows many advantages over known processes of dehydrogenation. For example, it greatly avoids the formation of oxygenated products, due to the fact that the presence of molecular oxygen is excluded. Moreover, hydrogen is eliminated as it is formed; by reacting with the oxygen in the metal oxide to form $H_2O$; thereby favorably displacing the equilibrium of the reaction and allowing the process to run at lower temperatures. The reaction of dehydrogenation is represented by:

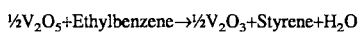

$$½V_2O_5 + \text{Ethylbenzene} \rightarrow ½V_2O_3 + \text{Styrene} + H_2O$$

Δ H=−18.78 KCal/Mole (exothermic).

Therefore, with the present invention it is no longer necessary to use diluents such as inert gases to favorably displace the equilibrium; however the process of the invention may also be carried out in the presence of the usual diluents.

Another distinct advantage of the process of the present invention resides in the fact that it is usable with quasiisothermal reactors at lower temperatures, while with the prior processes it was practically necessary to work under adiabatic conditions.

A substantial increase in the conversion rate and the yield rate in dehydrogenated hydrocarbons is also accomplished with the present invention. Further, it has been found that it is no longer necessary to work under a vacuum.

The process of the invention will be better illustrated by way of the following examples:

EXAMPLE 1

A. Preparation of the catalyst 11.21 g of ammonium metavanadate were dissolved in 200 ml of hot deionized water.

30 g of magnesium oxide powder were homogenized in 200 ml of water at 90° C. for 1 hour. The metavanadate solution was then added, and the resulting mixture was homogenized at 90 C. for another hour.

The mixture temperature was then raised to 120° C. and the excess water was evaporated for 18 hours under a nitrogen flow.

The resulting solid catalyst was calcined at 600° C. for 4 hours and then pelletized. The pellets were ground and sieved to give a $V_2O_5$-type catalyst, supported on magnesium oxide.

B. Catalytic dehydrogenation of ethylbenzene

Ethylbenzene was passed over 500 mg catalyst (as obtained from A) in pulses at a temperature of 505° C., under atmospheric pressure, the amount of ethylbenzene being 3.6 mg per pulse.

The following results were obtained:

conversion of ethylbenzene: 99.1 mol % styrene selectivity: 91.7 mol % yield: 90.9%

After the process had run long enough so that the conversion rate was reduced by about 10% below the initial conversion rate, ethylbenzene injections were stopped and the catalyst was regenerated by passing air over it in pulse mode at a temperature of 500° C.

After catalyst regeneration, ethylbenzene injections were resumed under the same conditions, and the following results were obtained:

conversion of ethylbenzene: 98.1 mol % styrene selectivity: 92.2 mol % yield: 90.4%

C. Comparative example

Using an adiabatic mode, a commercial catalyst for dehydrogenation of ethylbenzene, containing iron oxide, was used at a temperature of 600° C., under a pressure of 0.06 MPa, with a liquid hourly space velocity of 0.45, and in the presence of steam in a molar ration of $H_2O$/ethylbenzene of 8. The following results were obtained:

conversion of ethylbenzene: 70 mol % styrene selectivity: 90–92 mol % yield: 63–64.4%

This comparative example shows that a higher yield is obtained by the process of the invention, at lower temperatures and without having to add a diluent.

What is claimed is:

1. A process for the catalytic dehydrogenation of alkylaromatic hydrocarbons into the corresponding alkenylaromatic hydrocarbons, characterized in that it comprises the steps of:

a. contacting a hydrocarbon feedstock under dehydrogenation conditions, in the absence of any gas containing molecular oxygen, with a catalyst consisting of a reducible oxide of vanadium, supported on a material selected from the group consisting essentially of metallo silicate zeolite materials and metallo-aluminophosphate zeolite materials and oxides of a second metal selected from the group consisting essentially of Ti, Zr, Zn, Th, Mg, Ca, Ba, Si and Al; said catalyst having a dehydrogenation activity when said vanadium has a valency such that it is not in its most reduced state;

b. recovering dehydrogenated hydrocarbons;

c. regenerating the catalyst; and, d. repeating said steps a and b above.

2. The process of claim 1, characterized in that the catalyst is supported on an oxide selected from the group consisting of magnesium oxides and zinc oxides.

3. The process of claim 2, characterized in that said catalyst is supported on a zeolite material selected from the group consisting essentially of alumino-silicates, borosilicates and silico-alumino-phosphates.

4. The process of claim 1, characterized in that said dehydrogenation of alkylaromatic hydrocarbons and recovery of the catalysts are carried out in a fluidized bed reactor.

5. The process of claim 1, characterized in that said supported catalyst is regenerated by passing through the catalyst bed a gas containing molecular oxygen at a temperature of from 200° to 1000° C.

6. The process according the claim 1, wherein said supported catalyst is regenerated by passing through the catalyst bed a gas containing molecular oxygen at a temperature of from 200° to 1000° C. after a reduction of about 10% in the conversion of alkylaromatic hydrocarbons is observed.

7. The process of claim 1, wherein said catalyst recovered from the dehydrogenation reactor is regenerated by sending it into a second reactor wherein a molecular-oxygen-containing gaseous flow is passed through it at a temperature of from 200° to 1000° C., with a residence time of from about 5 seconds to about 5 minutes, and said catalyst is recovered for recycling to the dehydrogenation reactor.

8. The process of claim 7, wherein said second reactor is a fluidized bed reactor.

9. The process of claim 1, characterized in that the dehydrogenation reaction is carried out at a temperature of about 360° to about 800° C., at a pressure of from about 0.001 to about 1 MPa, and at an hourly space velocity between about 0.01 and about 10 kg of hydrocarbon per hour and per kg of catalyst.

10. The process of claim 9, wherein said temperature is between 400° and 650° C.

* * * * *

UNITED STATES PATENT AND TRADEMARK OFFICE
CERTIFICATE OF CORRECTION

PATENT NO. : 5,510,553

DATED : April 23, 1996

INVENTOR(S) : Delorme, et al.

It is certified that error appears in the above-identified patent and that said Letters Patent is hereby corrected as shown below:

On the title page, item [63], delete "1992" and insert --1993--.

Signed and Sealed this

Thirty-first Day of August, 1999

*Attest:*

Q. TODD DICKINSON

*Attesting Officer*      *Acting Commissioner of Patents and Trademarks*